United States Patent [19]

Herskowitz

[11] Patent Number: 5,330,431
[45] Date of Patent: Jul. 19, 1994

[54] INFUSION PUMP

[76] Inventor: Glenn Herskowitz, 425 Divisadero, Ste. 200, San Francisco, Calif. 94117

[21] Appl. No.: 30,782

[22] Filed: Mar. 12, 1993

[51] Int. Cl.⁵ .................. A61M 1/00; B65D 35/28
[52] U.S. Cl. .................. 604/153; 604/131; 222/101
[58] Field of Search ............. 604/153, 131, 151, 259, 604/262, 165; 222/101

[56] References Cited

U.S. PATENT DOCUMENTS

| D. 324,911 | 3/1992 | Sancoff | D24/111 |
|---|---|---|---|
| 3,647,117 | 3/1972 | Hargest | 604/131 |
| 3,670,926 | 6/1972 | Hill | 604/131 |
| 4,331,265 | 5/1982 | Warlick | 220/101 |
| 4,403,714 | 9/1983 | Kane | 222/101 |
| 4,666,430 | 5/1987 | Brown | 604/141 |
| 4,731,058 | 3/1988 | Doan | 604/155 |
| 4,741,736 | 5/1988 | Brown | 604/134 |
| 4,898,583 | 2/1990 | Borsanyi | 604/153 |
| 5,080,652 | 1/1992 | Sancoff | 604/132 |
| 5,105,983 | 4/1992 | Sancoff | 222/103 |

FOREIGN PATENT DOCUMENTS

| 511261 | 8/1976 | U.S.S.R. | 220/101 |
|---|---|---|---|
| 2204797 | 11/1988 | United Kingdom | 604/153 |

OTHER PUBLICATIONS

SideKick ™ brochure by I-Flow Corporation of Irvine, Calif. with Addendum, dated Jan. 4, 1993.
The McGaw READYMED ™ by McGaw, Inc. of Irvine, Calif. dated 1992.
Homepump ™ by Block Medical, Inc. of Carlsbad, Calif. dated prior to 1993.
Portable Infusion Systems by Baxter Healthcare Corporation of Deerfield, Ill. dated 1991.
CADD-PLUS © by Pharmacia Deltec Inc. of St. Paul, Minn. dated 1991.

Primary Examiner—John G. Weiss
Attorney, Agent, or Firm—Flehr, Hohbach, Test, Albritton & Herbert

[57] ABSTRACT

An infusion pump for use with standard pre-filled single dose IV bags. The pump includes a housing having a lid which opens and closes so that the IV bag can be inserted and supported in a delivery mode position. A platen surface is positioned along one side of the bag while a compression roller is mounted for movement along the other side of the bag. A control circuit actuates drive means which moves the compression roller in a direction towards a dispensing port of the bag while the roller applies force for expelling solution from the bag. Forward movement of the pressure roller is controlled to maintain solution pressure within the bag at a predetermined level. Electromechanical indicators, alarms and interlock features are provided for purposes of safety and for monitoring the infusion process.

5 Claims, 5 Drawing Sheets

INFUSION PUMP

BACKGROUND OF THE INVENTION

1. Field of the Invention

This invention relates in general to methods and apparatus for infusing intravenous ("IV") solutions. In particular, the invention relates to an infusion pump which is adapted for use with prepackaged, single dose containers for delivering solutions intravenously to patients.

2. Description of the Prior Art

Infusion pumps are used to deliver various types of solutions intravenously to patients. A variety of drugs are commonly administered to patients by means of the intravenous solutions. Among the types of therapies requiring this kind of administration are chemotherapy, antibiotic therapy and antiviral therapy. In many cases, patients receive multiple daily therapies. Certain medical conditions require infusions of drugs in solution over relatively short periods such as from 30 minutes to 2 hours. It is important that the solutions be administered accurately and completely. The different types of infusion pumps in the prior art include elastomeric pumps which squeeze the solution from flexible containers, such as balloons, into tubing for delivery to the patient. Spring loaded pumps have also been provided to pressurize the solution containers or reservoirs. Infusion pumps have also been provided with cartridges containing flexible compartments that are squeezed by pressure rollers for discharging the solutions, such as the pump shown in U.S. Pat. No. 4,741,736. These types of infusion pumps, however, require special containers and are not adaptable for using standard pre-filled single dose containers for IV solutions. Where infusion pumps cannot use the standard pre-filled single dose containers, it is necessary to separately compound the solution in large containers and transfer portions to the cartridges, balloons, reservoirs and other specialized containers. The requirement to compound and transfer the IV solution is time consuming, and because the work must be done by professionals, the cost is increased to the consumer. In addition, the requirement to manipulate the solutions and medications increases the risk of contamination in the preparation phase. This process also creates storage problems in that the compounded solution must be refrigerated, which further adds to the cost. The need has therefore been recognized for an infusion pump system which obviates the limitations and disadvantages of existing pumps of this type, and which is adapted for use with standard pre-filled single dose IV containers.

OBJECTS AND SUMMARY OF THE INVENTION

It is a general object of the invention to provide a new and improved infusion pump which is adapted for use with pre-filled single dose IV containers.

Another object is to provide an infusion pump of the type described which eliminates the need for the health care professional to separately compound and transfer the IV solution into containers used with the pump, and thereby minimize costly preparation steps.

Another object is provide an infusion pump of the type described which accurately dispenses the IV solution at a controlled pressure and for a controlled period of time.

Another object is to provide an infusion pump of the type described which includes a control system with safety features.

Another object is to provide an infusion pump of the type described which achieves health benefits by obviating the risk of contaminating the IV solution, obviating the need for refrigeration of the solution, and providing an alarm in the case where the solution is not completely delivered to the patient.

The invention in summary provides an infusion pump having a housing with a platen surface which supports a standard pre-filled single dose IV container bag. A compression roller in the housing applies a compression force against one sidewall of the bag with the other sidewall juxtaposed against the platen surface. The compression roller is driven toward the bag's discharge port while the compression force is applied for expelling solution from the bag. Control means is provided for controlling the drive to move the compression roller at a rate which maintains a predetermined level of pressure in the solution.

The foregoing and additional objects and features of the invention will appear from the following specification in which the several embodiments have been set forth in detail in conjunction with the accompanying drawings.

DESCRIPTION OF THE PREFERRED EMBODIMENTS

In the drawings FIGS. 1-4 illustrate generally at 10 an infusion pump according to a preferred embodiment of the invention. Infusion pump 10 provides an ambulatory system which enables health care professionals to infuse patients directly from standard 50 or 100 ml. single dose container bags which are pre-filled with IV solutions. The infusion pump of the invention is adaptable for use in homes, hospitals or clinics. It is readily adapted for operation in any position, such as resting on a table with the patient in bed, and it could also be carried by the patient.

Infusion pump 10 is comprised of a box-shaped housing 12 having a lid 14 which pivots open and closed about a pair of hinges 16, 18.

The typical IV bag 20 is comprised of a flexible, transparent plastic container with sidewalls 22, 24 of generally rectangular shape. The bag has a first end 26 molded with a pair of necks 28 (one of which is shown) which provide standard filling and dispensing ports. The second or tail end 30 of the bag (shown as a 50 ml. size bag) is formed with a standard hang hole 32.

Within the housing, means is provided for supporting IV bag 20 in its delivery position. The support means is comprised of a front housing wall 34 together with a forwardly inclined panel 36 which is an extension of flat horizontal plate 38 that supports the lid hinges. Preferably panel 36 inclines at an angle on the order of 45° with respect to the horizontal plate. The top edge of front wall 34 is formed with a pair of semi-circular grooves 72, 74 which are sized commensurate with the outer diameters of the necks 28 which form the filling and dispensing ports for the bag. The necks fit within the semi-circular grooves for supporting the front end of the bag in the manner explained below in connection with FIGS. 6 and 7.

The upper end of inclined panel 36 is formed with a rounded corner 42 providing a diaphragm surface which is shaped to support the underside of the tail end 30 of the bag. A pair of spring-loaded pegs 44, 46 are mounted in openings formed through panel 36 in alignment with the longitudinal centerline of the position occupied by the bag. The uppermost peg 44 is positioned for insertion through the hang hole 32 of a 50 ml. bag, and the lowermost peg 46 is positioned for insertion through the hang hole of a 100 ml. bag.

Figure 5:
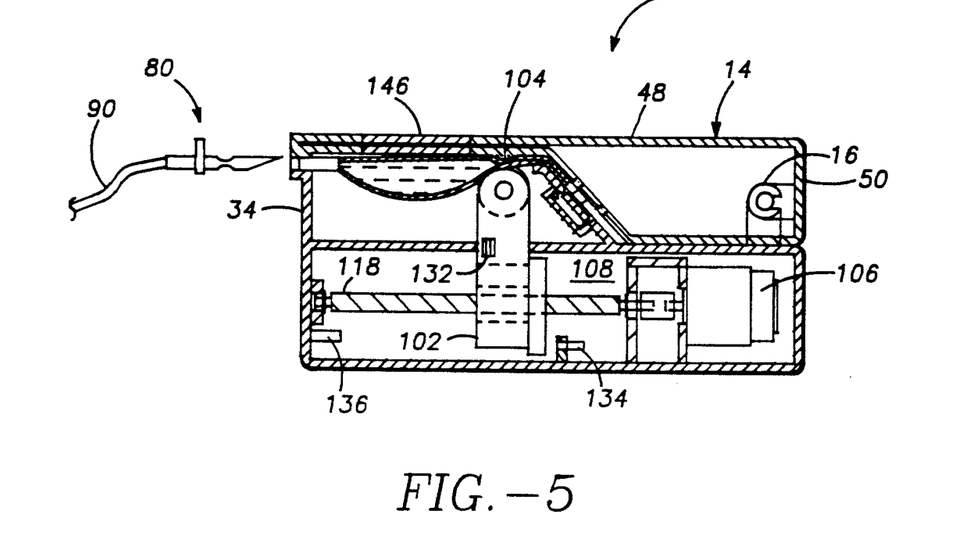
FIG. 5 is a longitudinal sectional view taken along the line 4—4 of FIG. 3 showing the pump with the lid closed and with the IV bag in its delivery position for dispensing solution.

Housing lid 14 is comprised of an upper panel 48, rear wall 50, lower panel 52, sidewalls 54, 56 and front wall 58. The sidewalls form a skirt which hangs down around the periphery of the front portion of the housing when the lid is closed. Lower panel 52 is formed with a portion 60 which inclines at an angle corresponding to that of inclined panel 36 on the housing so that these two parts are in juxtaposed relationship when the lid is closed, as illustrated in FIG. 5. Inclined portion 60 is also formed with a pair of openings 62, 64 which are positioned so that they are aligned with respective pegs 44 and 46 when the lid is closed. In the closed position of the lid, the pegs project at least partially into openings 62, 64 so that the tail end of the bag is releasably captured in the dispensing position shown in FIG. 5. When the lid is raised the health care professional can easily lift the bag's tail end off the pegs and pull the bag up to discard it and replace with another pre-filled bag, as required by the particular therapy procedure.

Figure 4:
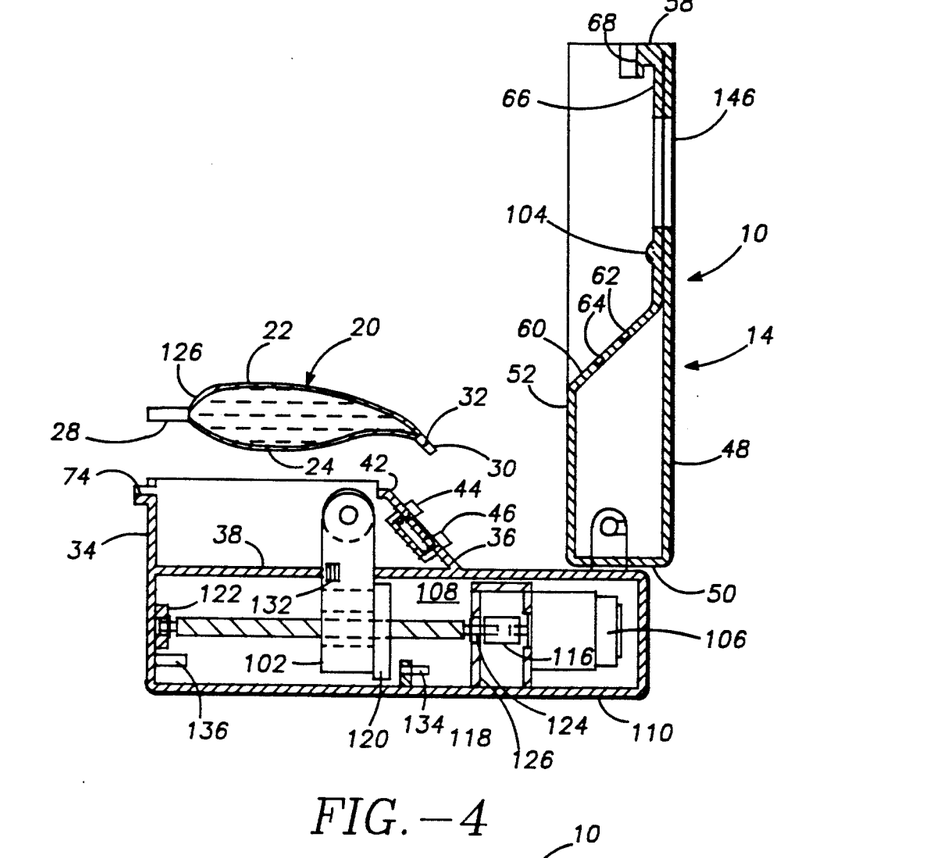
FIG. 4 is a vertical longitudinal section view of the pump of FIG. 2 with the lid open and showing one step in the method of inserting an IV bag into the pump.

Lower panel 52 of the lid includes a front portion 66 which is in contact across the lower surface of upper panel 48. The bottom of this front portion provides a platen surface which lies over the top sidewall of the IV bag when the lid is closed, as shown in FIG. 4.

Figures 1, 6, 7:
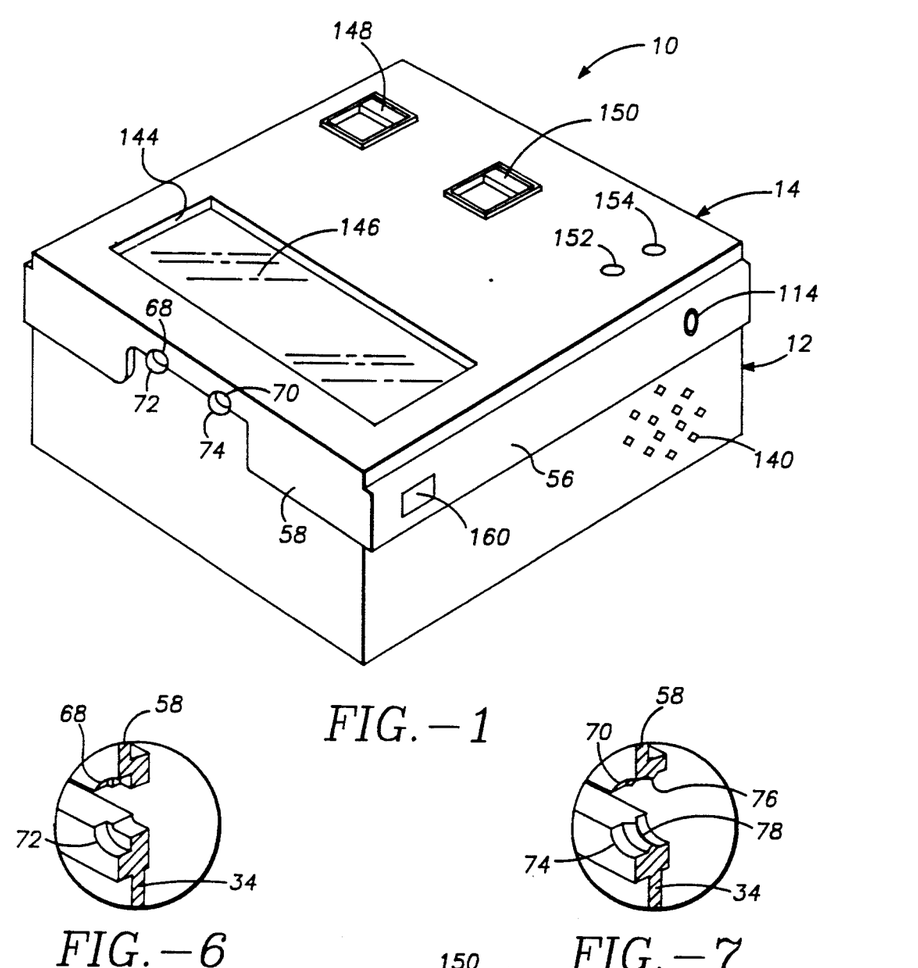
FIG. 1 is a perspective view illustrating the infusion pump in accordance with one embodiment of the invention.
FIG. 6 is an enlarged fragmentary perspective view of a portion of the lid and housing for the pump of FIG. 1 showing the structure for supporting the filling port of the IV bag.
FIG. 7 is an enlarged fragmentary perspective view of the portion of the lid and housing showing the structure for clamping the dispensing port of the IV bag.
Figure 2:
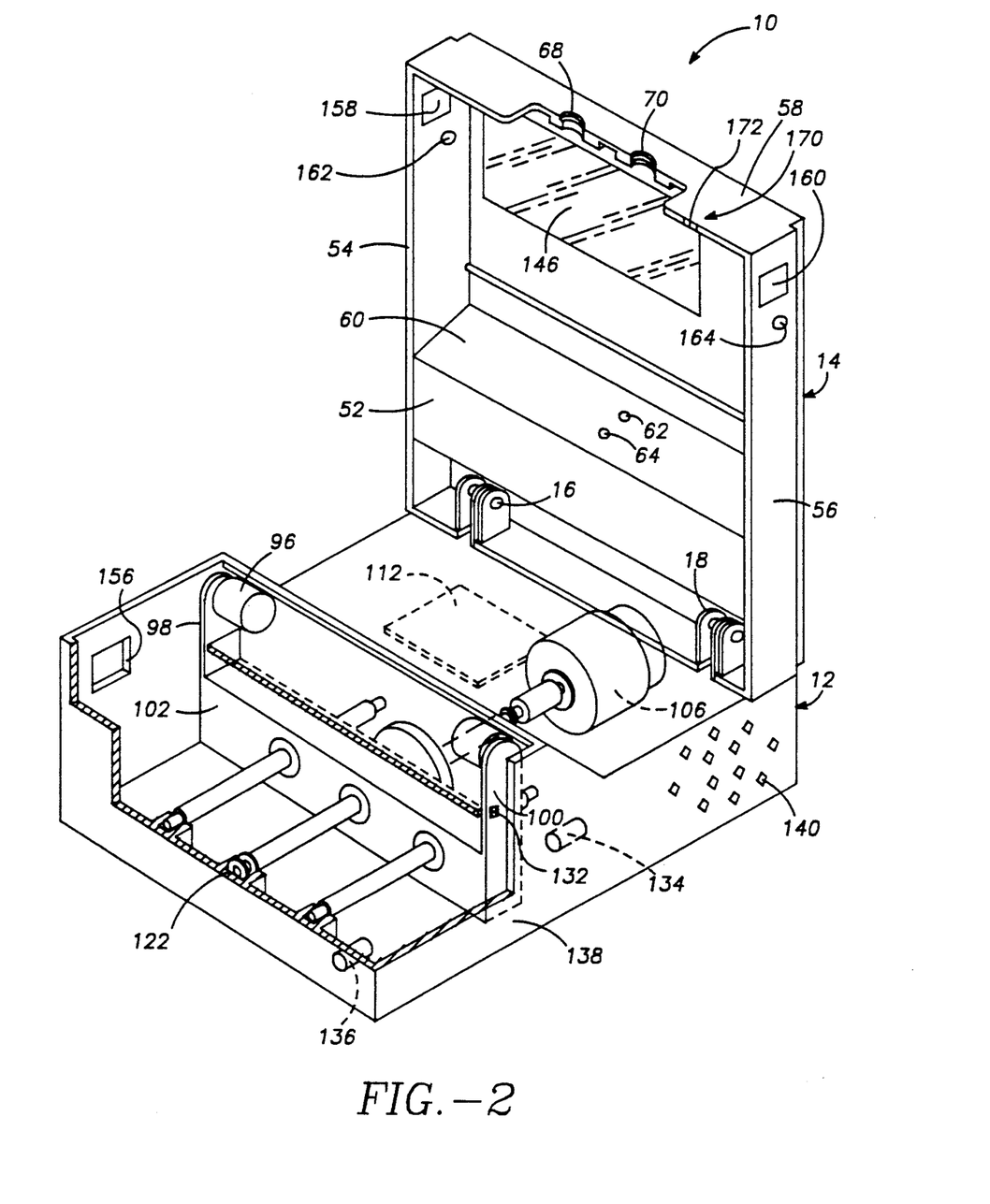
FIG. 2 is a perspective view, partially broken away, similar to FIG. 1 showing the pump lid in open position.
Figure 3:
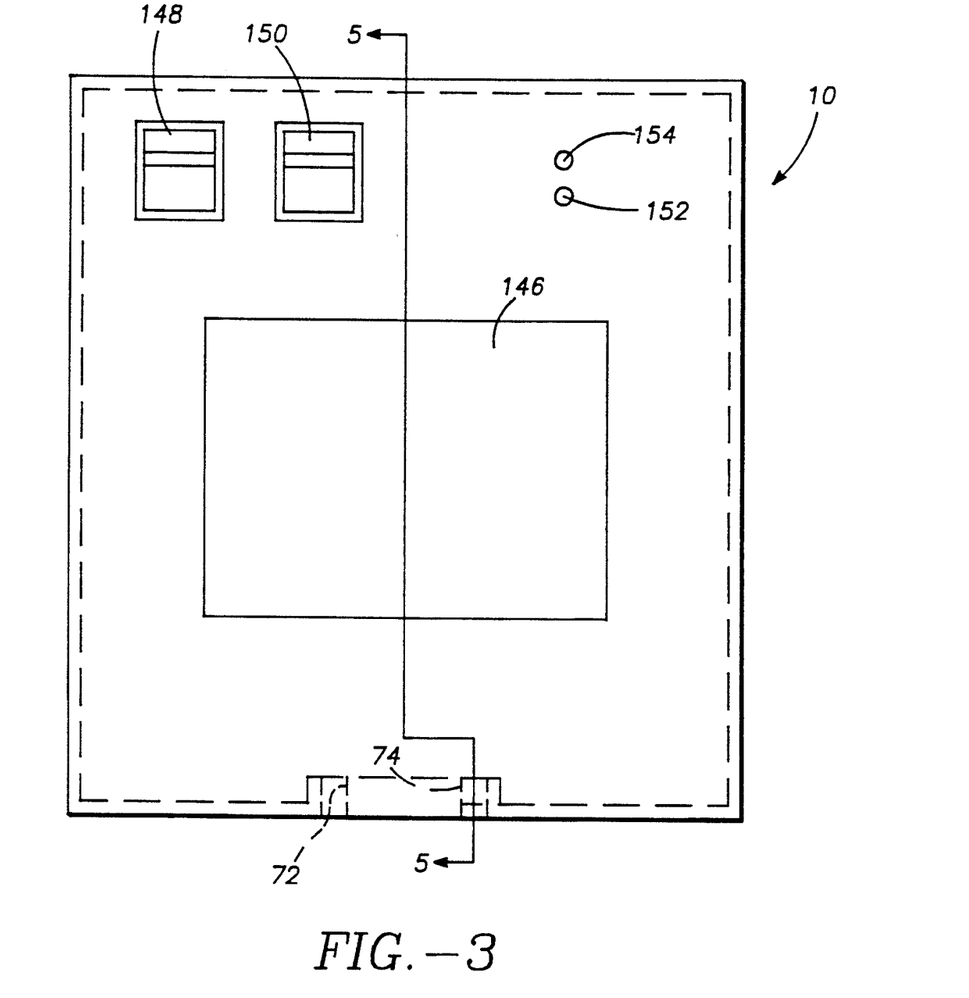
FIG. 3 is a top plan view of the pump of FIG. 1.
Figure 10:
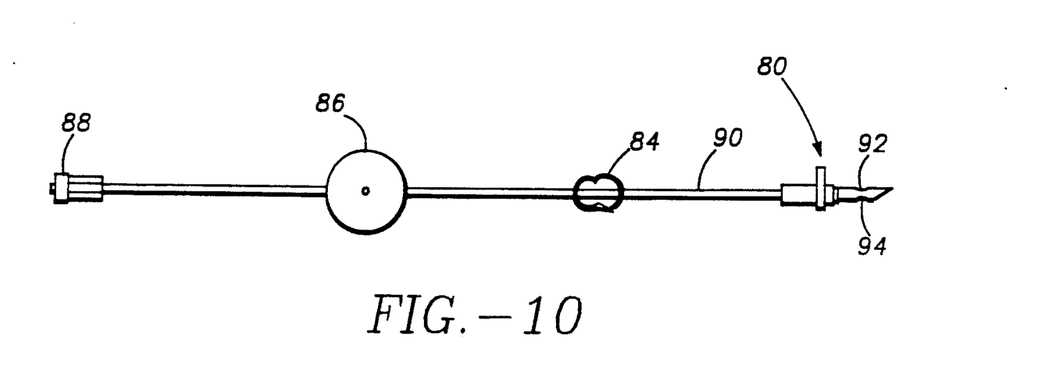
FIG. 10 is a side view of the IV tubing assembly used with the infusion pump of FIG. 1.

As best shown in FIGS. 2, 6 and 7, a pair of semi-circular grooves 68, 70 are formed through the lower edge of lid front wall 58. Aligned with these grooves are a pair of semi-circular grooves 72, 74 formed through the upper edge of housing front wall 34. Semi-circular locking ridges 76, 78 of triangular cross section are formed about the inside of respective grooves 70, 74. When the lid is closed, the matching grooves 70 and 74 cooperate to clamp about the neck 28 which forms the dispensing port of the bag. The locking ridges press into and lock with the spike 80 of IV tube assembly 82 as shown in FIG. 10. The dispensing port of the bag is accessible from outside the housing for connection with the IV tubing assembly which comprises the spike 80, on-off clamp 84, air venting filter 86, needle adapter 88 and low volume flow tubing 90. The tubing is sized with a predetermined diameter which serves as a flow restrictor to control the flow rate of solution from the IV bag to the patient. Alternatively, a suitable flow restrictor orifice, not shown, can be provided in the tubing assembly to control the flow rate. The spike is formed with a top recess 92 and bottom recess 94 which are shaped and sized commensurate with locking ridges 76 and 78. Closure of the lid forces these ridges into the spike recesses 92 and 94 to securely hold the tubing assembly. This provides an important safety feature preventing unintended removal of the spike and tubing from the infusion pump. Alternatively, the spike could be formed with ridges which match recesses formed in the semi-circular grooves.

Means is provided within the housing for applying a compression force against the side of the IV bag which faces downwardly when the bag is supported in its delivery mode position. This means comprises a compression roller 96 which extends laterally across the housing and is mounted for rotation between a pair of arms 98, 100 which extend upwardly from a carrier frame 102. The compression roller can be formed of a suitable yieldable material such as neoprene rubber. Arms 98 and 100 of the carrier frame hold the compression roller so that it pinches the flexible bag up against platen surface formed by front portion 66 of the closed lid.

FIG. 5 illustrates the home position of the compression roller after a fresh bag is inserted and prior to initiating the dispensing operation. When an IV bag is placed in its delivery mode position and the lid is closed, inclined portion 60 of the lid presses the bag tail end against forwardly inclined panel 36 of the housing. A transversely extending, downwardly projecting convex ridge 104 is formed across the platen surface of lid front portion 66. When the lid is closed, the ridge 104 is positioned slightly inboard of the compression roller, which is to the right of the roller as viewed in FIG. 5. In this position the roller pinches the bag tightly against the ridge. With both sidewalls of the bag pinched between the roller and ridge in this manner, counter flow of solution to the tail end of the bag is prevented. In addition, in this initial, home position of the roller, the pinching action pushes solution in the bag forward toward the dispensing port.

Rounded edge 42 of inclined panel 36 provides a diaphragm surface over which the bag tail end 30 bends. This bending action causes the bag sidewalls at the tail end to come together and force solution in the tail end forward. The flexible plastic sidewalls of the bag tend to bulge outwardly as the upward force of the compression roller pressurizes the solution. When the lid is closed the action of the diaphragm surface against the bag tail end as well as the pinching action of the compression roller pushing the bag upwardly against ridge 104 pressurizes the solution for an initial flushing of the tubing assembly prior to starting the drive for the roller.

Drive means is provided for moving carrier frame 102 forwardly toward the discharge port while the compression roller applies force for expelling solution from the bag. The drive means comprises a micromotor 106 mounted in the compartment 108 formed below flat plate 38 and bottom wall 110 of the housing. The micromotor is driven by a suitable electrical power source, such as a standard 9-12 VDC battery 112, which can be of the rechargeable type. A DC adaptor/recharger jack 114 is provided on the lid sidewall 56 for recharging the battery. The micromotor provides the requisite torque for moving carrier frame 102 back and forth by means of a drive train comprising a coupling 116, lead screw 118 and threaded lead screw collar 120 which is mounted on the carrier frame. The front end of the lead screw is mounted to the front wall of the housing by a support bearing 122, and the rear end of the lead screw is mounted through a support bearing 124 to a bracket 126 which also carries the drive coupling. A pair of guide pins 128, 130 extend between the housing front wall and bracket 126. The guide pins are mounted parallel with and on opposite sides of the lead screw for purposes of stabilizing movement of the carrier frame. The guide pins also prevent excessive downward forces from being applied to the lead screw from the fluid pressure built up in the IV bag. As explained in more detail below in connection with the control circuit 131 of FIG. 8, pressure of the solution within the bag is controlled at a predetermined level by controlling the rate of movement of the compression roller toward the dispensing port. The level of solution pressure is sensed and fed back to the control circuit by means which includes a strain gauge sensor 132 mounted on arm 100 of the carrier frame. Suitable electric leads, not shown, connect strain gauge sensor 132 into the circuit of FIG. 8.

Flat plate 38 extends between the carrier frame arms above the driving mechanism and other components in lower compartment 108 to protect these components from contact with the IV bag as well as from the hands and fingers of the health care professional and patient. Within the lower compartment a first proximity sensor 134 is mounted to sense the position of the carrier frame at its home position, shown in FIGS. 3 and 4. A second proximity sensor 136 is mounted at the forward end of the lower compartment for sensing the extreme forward position of the carrier frame at the end of the dispensing phase. The proximity sensors are connected for operation in control circuit 131 as explained below in connection with FIG. 8.

On one sidewall 138 of the housing a cluster of openings 140 is provided for sound ports for a speaker 142 which is mounted within compartment 108. The speaker is connected with control circuit 131 of FIG. 8. The control circuit actuates the speaker to provide audible indicators of operating conditions.

An opening 144 is formed through lid upper panel 48 and front portion 66 for mounting a clear window 146. The window permits the health care professional and/or patient to view the bag and monitor the infusion procedure. The window is made of a suitable rigid plastic material which is sufficiently strong to serve as the platen surface and resist pressure forces acting on the bag. A power on/off/reset slide switch 148 is mounted in the top of the housing. This switch is of the type which includes a colored lamp, preferably a green light emitting diode 176 (LED), for visual indication of the control process. The lid also mounts an infusion start slide switch 150. This switch is of the type which includes a lamp of a different color, preferably a yellow LED 184. On the lid a colored indicator lamp 152, preferably a red LED, is provided to indicate an excessive pressure condition, and another colored indicator lamp 154, preferably an orange LED, is provided to indicate a low battery condition.

Means is provided for releasably locking lid 14 in its closed position on the housing. This means includes a rectangular opening 156 formed at the front of each sidewall of the housing. At the forward ends of the lid sidewalls 54 and 56 a pair of inwardly projecting spring-loaded detents 158 and 160 are pivotally mounted in positions which match with the housing openings when the lid is closed. The detents pivot inwardly and engage the openings when the lid is closed, and the detents can be manually operated to pivot out and disengage from the openings so that the lid is released for moving back to its raised position.

The inside surfaces of the lid sidewalls mount on one side an LED 162 of the type which emits a beam of infrared light, and on the other side a phototransistor 164 which responds to light from the LED. The LED and phototransistor cooperate to serve as presence detectors and are positioned in optical alignment to detect the bag when it is in its delivery mode position with the lid closed. The LED and phototransistor presence detectors are connected with a bag-in-place switch 166 in the control circuit of FIG. 8. The switch 166 is closed through activation of the phototransistor when the bag is in proper place. A cover closed switch 168 in the circuit is closed by a sensor switch 170 which operates when the lid is fully closed. The sensor switch is comprised of a first thin film switch component 172 mounted on the lower edge of the lid front wall 58, and a second thin film switch component, not shown, mounted on the top edge of housing front at a position where the two film components are in juxtaposed relationship when the lid is fully enclosed.

Figure 8:
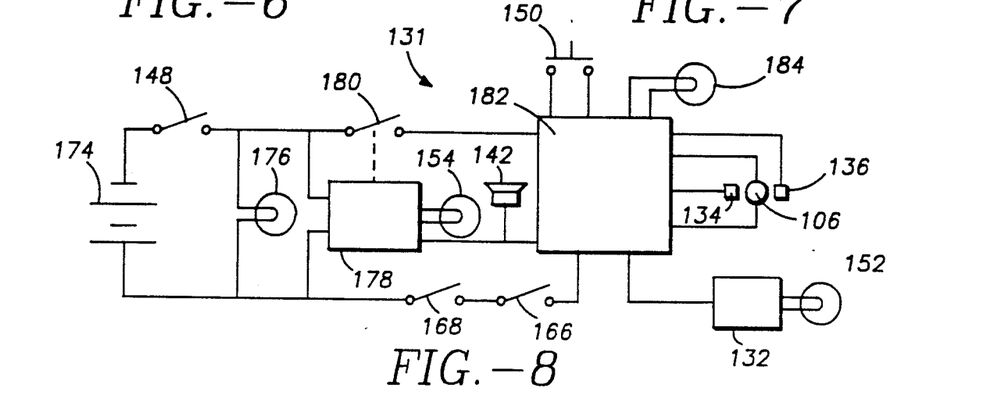
FIG. 8 is a circuit diagram of the control system in the pump of FIG. 1.

FIG. 8 schematically illustrates details of control circuit 131 which controls operation of infusion pump 10. The on/off switch 148 is connected to one terminal of battery 174. Green LED 176 is connected in the circuit and lights when switch 148 is closed. A battery test circuit 178 is connected in the circuit for sensing battery charge condition. When the charge is sensed below a predetermined level, orange LED 154 is lit. Battery interlock switch 180 is closed by circuit 178 when the charge is above the predetermined level. When the battery charge is insufficient for proper operation, interlock switch 180 is opened by the test circuit. The control circuit includes a motor controller printed circuit board (PCB) 182. Cover closed switch 168 and bag-in-place switch 166 are connected in series between one terminal of battery 174 and PCB 182.

When cover closed switch 168 is closed and bag-in-place switch 166 is also closed the circuit is closed between battery 174 and PCB 182. The PCB also connects through leads with infusion start switch 150, yellow LED 184 of switch 150, roller end sensor 136, micromotor 106, roller home sensor 132 and pressure strain gauge sensor 134. PCB 182 includes a suitable IC chip, not shown, which is programmed with appropriate conventional logic circuits to provide the functions described below in connection with the flow chart of FIG. 9.

Figure 9:
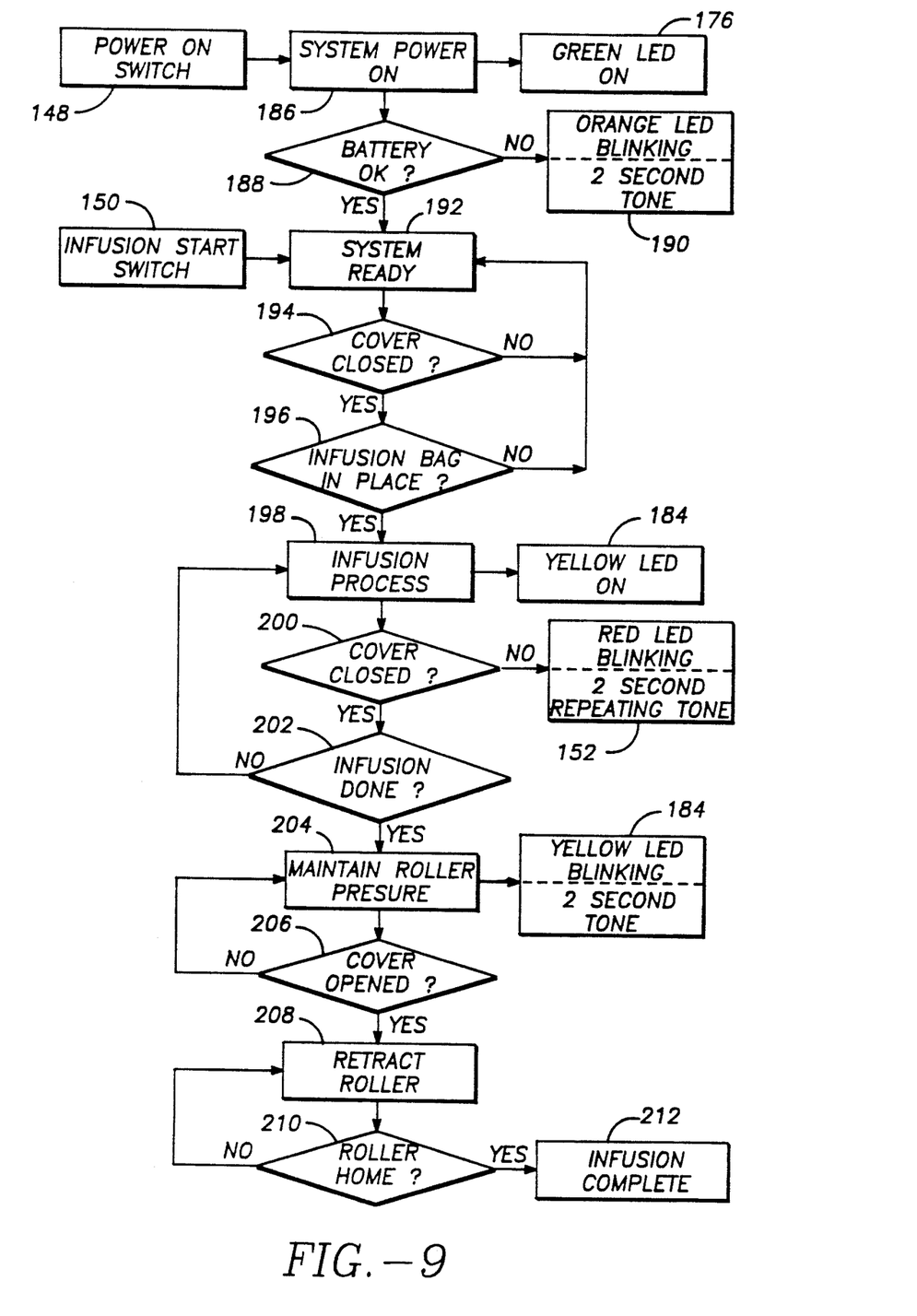
FIG. 9 is a flow chart illustrating the method steps in the operation of the control system of FIG. 8.

The steps in the method of operation of the control circuit and infusion pump of the invention will be explained in connection with the flow chart of FIG. 9. With power switch 148 turned on at step 186, the logic circuit in the IC chip of PCB 182 senses this condition and turns green LED 176 on. For the next step 188 the circuit checks the battery charge condition. If the charge is below the predetermined level, orange LED 154 blinks and speaker 142 is energized to give a two-second duration tone. If the battery charge is adequate, the logic goes to the system ready step 192. At this step if infusion start switch 150 has been turned on by the operator, the circuit checks to determine if the lid or cover is closed. If sensor 170 senses that the lid is closed at step 194, then the logic proceeds to the infusion bag-in-place step 196. If bag-in-place switch 166 is closed then the logic proceeds to the infusion process step 198, turning yellow LED 184 on. At the same time, micromotor 106 is energized so that lead screw 118 is turned to advance carrier frame 102 and compression roller 96 in a direction toward the front of the housing.

At step 198 as the roller begins its advance and squeezes the bag sidewalls together, fluid pressure begins to build up in the bag. The reaction force acting downwardly from this pressure against the compression roller is carried through the arms 98 and 100, and this force is sensed by strain gauge sensor 132 at step 200. The control signal from the strain gauge sensor is fed back into the IC chip within PCB 182. The control circuit continues to operate the micromotor so that the pressure roller advances until the feedback signal from the strain gauge indicates that the desired pressure level within the bag has been achieved. The micromotor is thereafter controlled on and off so that the roller is intermittently advanced at a rate which maintains the pressure, as predetermined by the size of the tubing or of any flow restrictor orifice in IV tubing assembly 82. If the pressure being sensed by sensor 132 goes above the predetermined level, then the logic at step 200 blinks red LED 152 while at the same time speaker 142 is actuated for a series of repeating two-second tones. These visual and audible signals serve to warn the operator of an unsafe condition. For example, an unsafe high pressure condition can occur where the clamp 84 in the IV tubing assembly has accidentally been left closed as infusion starts.

At the "Infusion Done?" step 202 roller end sensor 136 is actuated when carrier frame 102 reaches the forward end of its travel with the solution substantially dispensed from the bag. At step 204 roller pressure is still being sensed by strain gauge sensor 132 so that the control circuit blinks yellow LED 184. At the same time the speaker is activated to emit a steady high frequency tone. This indicates that the infusion process has been completed so that the operator can close clamp 84 to prevent back flow of fluid in the IV tubing, which could otherwise occur if the pressure roller retracts without the operator first closing the clamp. In the "Cover Open?" step 206, the control circuit generates a feedback circuit to maintain the yellow LED light and speaker tone as long as cover switch 168 remains closed. When the lid is opened so that the cover switch is opened, the compression roller is automatically retracted as the logic proceeds to the "Retract Roller?" step 208. Micromotor 106 is actuated in step 208 to turn the lead screw in a reverse direction, thereby retracting the carrier frame and compression roller. At the "Roller Home?" step 210, the logic provides a feedback signal to continue micromotor operation until proximity sensor 134 senses that the carrier frame has reached its home position. The micromotor is then deactivated at "Infusion Complete" step 212, and yellow LED 184 is switched off to indicate that the spent bag can be removed.

It is apparent from the foregoing that the present invention provides an infusion pump capable of using standard prepackaged single dose IV solution bags in a process which is safe, effective and relatively inexpensive. The process eliminates the cost of separately compounding and transferring solutions, and also minimizes the risks of solution contamination. It incorporates a number of safety features through a system which controls each of the steps of the infusion process. It dispenses solution under pressure at a constant flow rate for designated periods of time, and provides greater dispensing accuracy than infusion systems such as elastomeric pumps. Visual indicators and audible alarms are provided so that the process can be monitored. The infusion pump is also relatively compact and lightweight so that it can be used by an ambulatory patient.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. An infusion pump for use with a flexible bag containing a prepackaged intravenous solution, said bag having first and second ends and first and second sidewalls, the first end having a dispensing port adapted for discharging the solution through intravenous tubing for delivery to a patient, said pump comprising the combination of a housing, support means carried by the housing for supporting said bag in a delivery mode position, platen means carried by the housing for providing a platen surface which is positionable along said first sidewall of the bag, compression roller means within the housing for applying a compression force against said second sidewall of the bag with the first sidewall juxtaposed against said platen surface for producing pressure in said intravenous solution within the bag, drive means for moving the compression roller in a direction toward said dispensing port of the bag while said compression force is being applied for expelling solution from the bag through the dispensing port, and control means for controlling the drive means to move the compression roller in said direction for controlling said pressure in the solution, said control means including means for sensing the level of fluid pressure of the solution within the bag, and means responsive to said means for sensing the level of fluid pressure for operating said drive means to move the compression roller at a rate toward said dispensing port which maintains said fluid pressure substantially at a predetermined level.

2. An infusion pump for use with a flexible bag containing a prepackaged intravenous solution, said bag having first and second ends and first and second sidewalls, the first end having a dispensing port adapted for discharging the solution through intravenous tubing for delivery to a patient, said pump comprising the combination of a housing, support means carried by the housing for supporting said bag in a delivery mode position, platen means carried by the housing for providing a platen surface which is positionable along said first sidewall of the bag, compression roller means within the housing for applying a compression force against said second sidewall of the bag with the first sidewall juxtaposed against said platen surface for producing pressure in said intravenous solution within the bag, drive means for moving the compression roller in a direction toward said dispensing port of the bag while said compression force is being applied for expelling solution from the bag through the dispensing port, control means for controlling the drive means to move the compression roller in said direction for controlling said pressure in the solution, said housing including a base and lid and means for mounting the lid for movement between open and closed positions relative to the base, together with means for releasably holding an end of said intravenous tubing against displacement from said housing when the lid is moved to its closed position and when said end of the tubing is positioned in solution-receiving relationship with said dispensing port of the bag, said means for releasably holding said end of the intravenous tubing including first groove means formed in said lid and second groove means formed in said base with said first and second groove means being in juxtaposed relationship when the lid is moved to its closed position and with said end of the intravenous tubing being insertable within a portion of said dispensing port which is in seated position between the first and second groove means when said groove means are in said juxtaposed relationship.

3. An infusion pump as in claim 2 for use with intravenous tubing having a filling spike which is formed with a recess, said pump further comprising means forming a ridge on said first groove means with the dispensing port and said spike of the intravenous tubing being pressed together in clamping relationship between said ridge and recess when the lid is in its closed position.

4. An infusion pump as in claim 2 for use with intravenous tubing having a filling spike which is formed with a recess, said pump further comprising means forming an additional ridge on said second groove means with the dispensing port and said spike of the intravenous tubing being pressed together in clamping relationship between said additional ridge and recess when the lid is in its closed position.

5. A method of infusing intravenous solution from a flexible bag through tubing into a patient, the bag having first and second ends with the first end having a dispensing port adapted for discharging solution, the method comprising the steps of holding the second end of the bag in a fixed position, bending the bag over a diaphragm having a curved surface with the sidewalls of the bag adjacent the second end being brought together over the curved surface with the solution contained therebetween being forced towards said first end, holding said first end of the bag in a delivery position with an end of the tubing inserted in said dispensing port, applying a compression force between the sidewalls of the bag to pressurize the solution therein for forcing the solution through the dispensing port and into the tubing, the step of applying the compression force including holding said side walls of the bag between a platen surface and a compression roller while forcing the compression roller toward the platen surface, and a step of sensing solution pressure within the bag and controlling movement of the compression roller toward said dispensing port at a rate which is predetermined function of the pressure which is sensed in the solution.

* * * * *